(12) United States Patent
Nakai et al.

(10) Patent No.: US 7,713,197 B2
(45) Date of Patent: May 11, 2010

(54) PRESSURE MEASURING METHOD, PRESSURE MEASURING DEVICE, AND TONOMETER

(75) Inventors: Makoto Nakai, Tokyo (JP); Sunao Takeda, Ichikawa (JP); Akihiko Uchiyama, Yokohama (JP); Kenji Yanashima, Ichikawa (JP); Akihiro Fujita, Hamamatsu (JP); Itaru Yoshizawa, Tokyo (JP)

(73) Assignees: Waseda University, Tokyo (JP); Kowa Company, Ltd., Aichi (JP)

( * ) Notice: Subject to any disclaimer, the term of this patent is extended or adjusted under 35 U.S.C. 154(b) by 0 days.

(21) Appl. No.: 11/578,910

(22) PCT Filed: Mar. 18, 2005

(86) PCT No.: PCT/JP2005/004916
§ 371 (c)(1),
(2), (4) Date: Oct. 19, 2006

(87) PCT Pub. No.: WO2005/102150
PCT Pub. Date: Nov. 3, 2005

(65) Prior Publication Data
US 2007/0197893 A1    Aug. 23, 2007

(30) Foreign Application Priority Data
Apr. 23, 2004    (JP) .............................. 2004-128423

(51) Int. Cl.
*A61B 3/16* (2006.01)
*G01L 7/00* (2006.01)
*G01L 9/00* (2006.01)
*G01L 11/00* (2006.01)
*G01L 13/00* (2006.01)
*G01L 15/00* (2006.01)
*G01L 17/00* (2006.01)
*G01L 19/00* (2006.01)
*G01L 21/00* (2006.01)
*G01L 21/02* (2006.01)

(52) U.S. Cl. ...................... 600/402; 600/398; 702/138; 702/139

(58) Field of Classification Search ......... 600/398–406; 702/138, 139; 73/570–562, 721, 760–860
See application file for complete search history.

(56) References Cited

U.S. PATENT DOCUMENTS 3,192,765 A    7/1965    Keiper (Continued)

FOREIGN PATENT DOCUMENTS

EP    0061777    10/1982

(Continued)

OTHER PUBLICATIONS

Ujiie, et al. "Basic Experiment of Parameter Measurement for Muscle Stiffness by Contact Impedance Method," The Institute of Electronics, Information and Communication Engineers Gijutsu Kenkyu Hokoku, vol. 92, No. 310, pp. 47-52, Nov. 19, 1992.

(Continued)

*Primary Examiner*—Max Hindenburg
*Assistant Examiner*—John Pani
(74) *Attorney, Agent, or Firm*—Knobbe Martens Olson & Bear LLP

(57) ABSTRACT

A tonometry device includes a contact device for contacting the object, means for vibrating the contact device and the object, means for applying a voltage to the vibration means, means for measuring a current flowing through the vibration means, and an information processing means. The information processing means determines two resonance points of the device and the measured object by measuring current through the system at a plurality of vibrational frequencies. The information processing means then determines the internal pressure of the object by determining that a first pressure is higher than a second pressure by determining that the first pressure has a lower measured current than the second pressure at frequencies outside of the range of frequencies between the resonance points, and that the first pressure has a higher measured current than the second pressure at frequencies within the range of frequencies between the resonance points.

10 Claims, 13 Drawing Sheets

U.S. PATENT DOCUMENTS

| | | | |
|---|---|---|---|
| 4,597,288 | A * | 7/1986 | Kyogoku et al. ............... 73/384 |
| 4,646,754 | A * | 3/1987 | Seale .......................... 600/402 |
| 5,766,137 | A | 6/1998 | Omata |
| 5,830,139 | A | 11/1998 | Abreu |
| 6,800,061 | B1 | 10/2004 | Eklund et al. |
| 2002/0193675 | A1 | 12/2002 | Rathjen |
| 2004/0097799 | A1 | 5/2004 | Uchiyama et al. |

FOREIGN PATENT DOCUMENTS

| | | |
|---|---|---|
| EP | 0 764 842 A | 3/1997 |
| EP | 1 374 759 A1 | 1/2004 |
| JP | 01-162166 | 6/1989 |
| JP | 08-322803 A | 12/1996 |
| JP | 2004-267299 | 9/2004 |
| WO | WO 01/15594 A | 3/2001 |
| WO | WO 02/100260 | 12/2002 |
| WO | WO 02/100260 A | 12/2002 |

OTHER PUBLICATIONS

International Search Report dated Apr. 6, 2005.
Office Action in Russian Application No. 2006141351/14(045153) filed Nov. 22, 2006.
European Search Report issued on Jun. 29, 2009 for corresponding EP Application No. 05721103.9.
Eklund et al. "A resonator sensor for measurement of intraocular pressure- evaluation in an in vitro pig-eye model; Resonator sensor measurement of IOP." *Physiological Measurement: Institute of Physics Publishing.* 21(3):355-367 (2000).

* cited by examiner

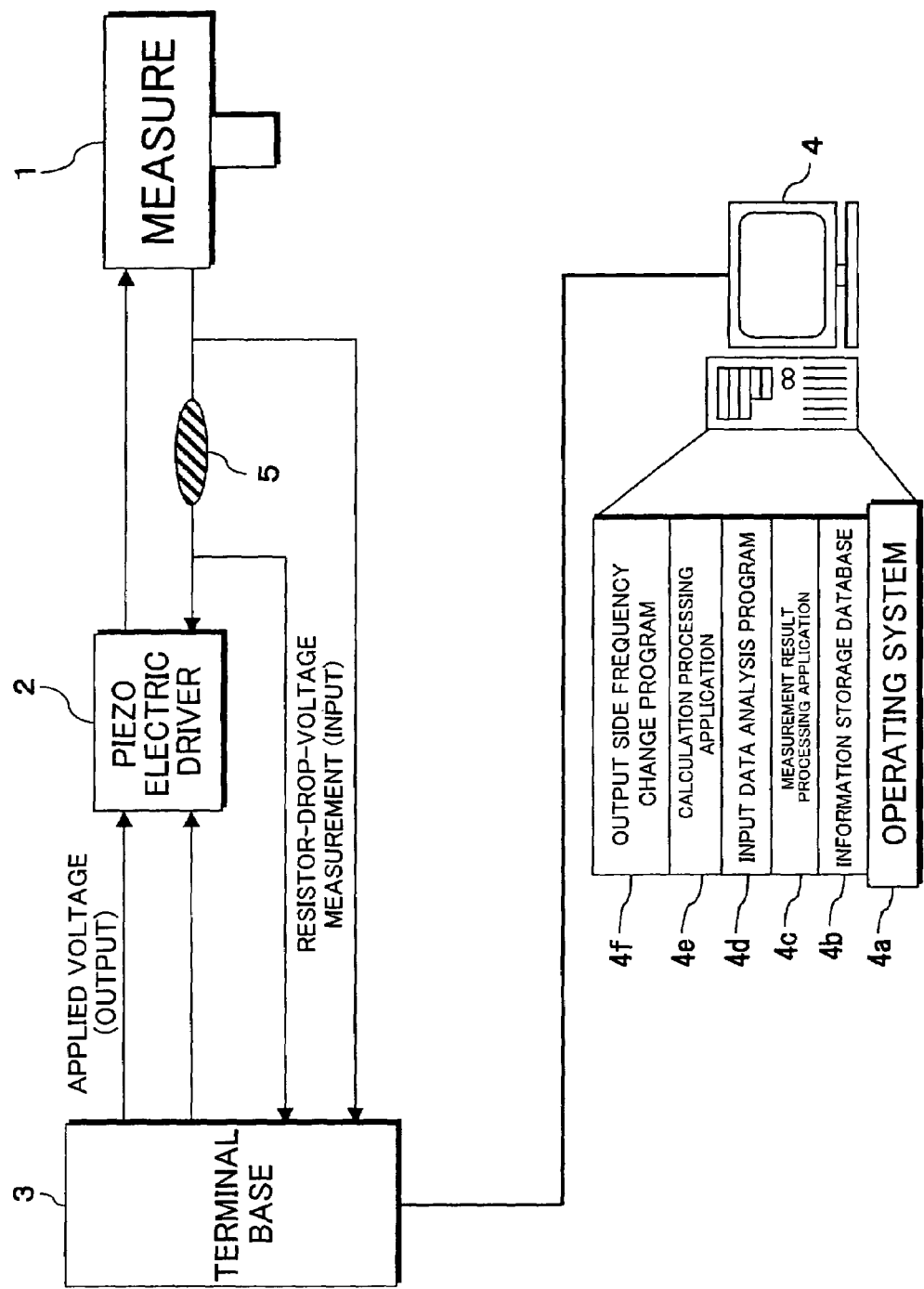

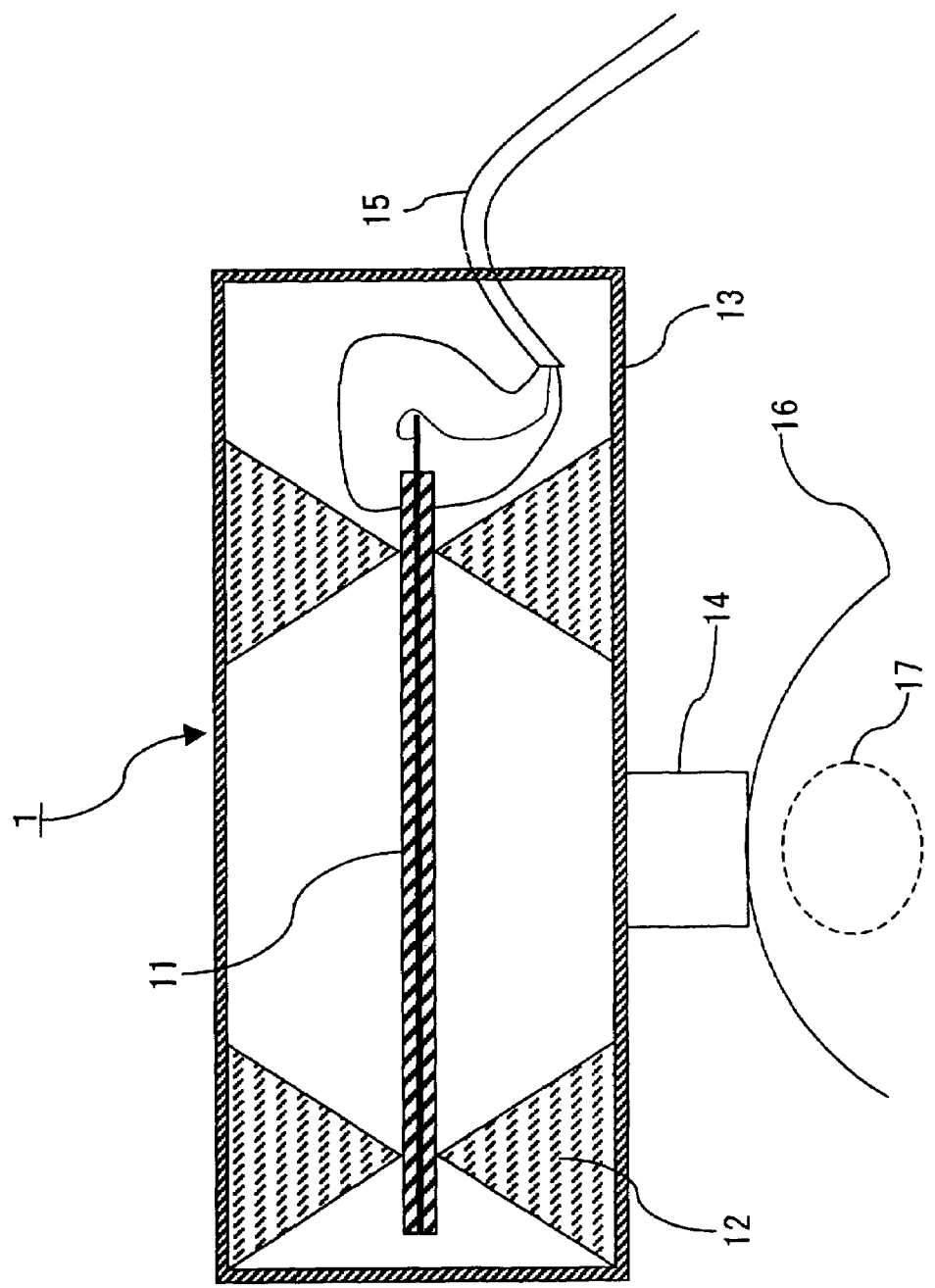

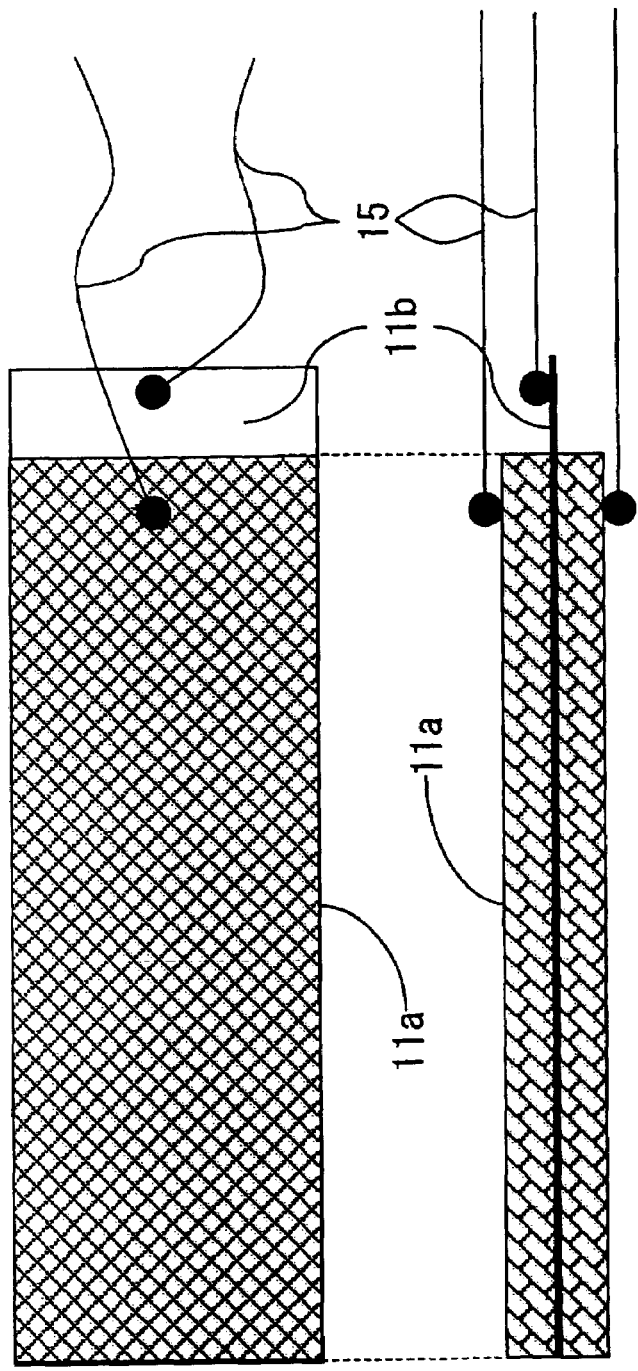

PRESSURE MEASURING METHOD, PRESSURE MEASURING DEVICE, AND TONOMETER

RELATED APPLICATIONS

This application is the U.S. National Phase under 35 U.S.C. §371 of International Application PCT/JP2005/004916, filed Mar. 18, 2005, which was published in a non-English language, which claims priority to JP Application No. 2004-128423, filed Apr. 23, 2004.

TECHNICAL FIELD

The present invention relates to a pressure measuring method, a pressure measuring device, and a tonometer, which are particularly suitable to be applied to an intraocular pressure measuring technique used for an ophthalmological examination.

BACKGROUND ART

The following two methods are generally known as intraocular pressure measuring methods. To be specific, there are employed a method of applying a predetermined pressure to a cornea to measure an intraocular pressure based on a depression state of the cornea, which is caused by the pressure and a method of estimating an intraocular pressure by bringing a presser into contact with the cornea (i.e., contact type) or by blowing compressed air to the cornea, based on an area ratio of the cornea deformed by the air pressure.

However, in those methods, the cornea is directly stimulated, so a high level of safety is required. In addition, a person to be examined has to bear a large burden such as a necessity of local anesthesia or discomfort feeling caused by air blowing.

Therefore, in order to solve such the problems, various methods have been proposed. That is, examples of the proposals include a method of vibrating a surface of an eyeball by a sound wave and measuring an intraocular pressure based on an amplitude of the vibration, a resonance frequency of the eyeball, or a velocity of a surface wave of the eyeball (see JP 02-180241 A, U.S. Pat. No. 5,375,595, and U.S. Pat. No. 5,251,627) and a method of pressing an eyeball in a closed-eye state through the eyelid to measure an intraocular pressure (see JP 06-105811 A, JP 08-280630 A, and JP 08-322803 A).

DISCLOSURE OF THE INVENTION

Problems to be Solved by the Invention

However, the above-mentioned conventional pressure measuring methods and tonometers as devices therefor have the following problems. That is, the method of bringing the presser into direct contact with the cornea requires anesthesia or the like and causes the person to be examined to feel discomfort or pain.

The methods described in JP 02-180241 A, U.S. Pat. Nos. 5,375,595, and 5,251,627 also cause the person to be examined to feel discomfort or pain because the intraocular pressure measurement is performed in an opened-eye state. Pressure measuring devices itself are large in sizes and directly stimulate the cornea, so a high level of safety is required. Therefore, an examiner must be a doctor or a medical worker.

JP 06-105811 A, JP 08-280630 A, and JP 08-322803 A disclose methods of performing an examination under such a state that the eyelid is closed, that is, a closed-eye state. According to the findings of the inventors of the present invention, the reproducibility of results obtained by the intraocular pressure measurement using the methods is insufficient.

Therefore, there has been an increasing desire for developments of techniques capable of measuring a pressure such as an intraocular pressure without causing the person to be examined to feel discomfort or pain and of easily measuring a pressure such as an intraocular pressure by the person to be examined with high reproducibility.

Thus, an object of the present invention is to provide a pressure measuring method capable of measuring a pressure in a simple measurement manner with high reproducibility and a pressure measuring device capable of measuring an intraocular pressure by merely making slight contact with the eyelid in the case where it is applied to an intraocular pressure measuring device (tonometer), accurately measuring a pressure by a simple method without causing discomfort or pain to the person to be examined, and measuring an intraocular pressure by the person to be examined.

Means for Solving the Problems

In order to solve the above-mentioned problems involved in conventional techniques, the inventors of the present invention conducted concentrated studies. The summary will be described below.

That is, according to the findings of the inventors of the present invention, in the above-mentioned conventional techniques, a load applied to the cornea during intraocular pressure measurement causes discomfort. Therefore, the inventors of the present invention studied methods of performing the intraocular pressure measurement with the state in which the eyelid is closed without the application of load to the cornea.

As a result of the studies, the inventors of the present invention came up with the use of a vibrator. That is, as a result of various experiments and studies based thereon, the inventors of the present invention found that there is a characteristic that, while a predetermined alternating current voltage is being applied to a vibrator such as a bimorph type vibrator to continuously drive it, a current flowing through the vibrator is changed corresponding to a material which is in contact with the vibrator. As a result of further experiments and studies based on this finding, the inventors of the present invention concluded that, a value of current flowing through the vibrator is changed according to an intraocular pressure while an eyeball is vibrated by the vibrator, so the intraocular pressure can be measured by the measurement of the current value.

The present invention has been devised based on the above-mentioned studies.

That is, the present invention is characterized in that a pressure measuring device in which vibration means can be in direct or indirect contact with an object to be measured is used, a voltage is applied to the vibration means to vibrate the vibration means together with the object to be measured, a current value changed according to a vibration amplitude of the vibration means is measured, and a pressure of the object to be measured is calculated based on the measured current value.

To be specific, a first aspect of the present invention, there is provided a pressure measuring method, including:

bringing vibration means, which is connected with contact means for making contact with an object to be measured and vibrated by an application of a voltage, into contact with an object to be measured through the contact means, in which the object to be measured has a predetermined shape and a pressure is applied in an outward direction from the object to be measured;

applying a voltage to the vibration means by voltage applying means for applying an alternating current voltage to the vibration means;

measuring a current value flowing through the vibration means by measuring means for measuring the current value flowing through the vibration means; and calculating the pressure based on the measured current value.

The first aspect of the invention, in a typical case, a resonance point of the object to be measured is calculated by information processing means based on a change in the current value which is caused by a change in vibration frequency, and the pressure based on a current value at a region of the resonance point is measured.

In the first aspect of the present invention, it is suitable to use a reference object to be measured as a reference for correcting a change in measurement value which is caused by a temperature characteristic of the vibrator, perform pressure measurement on the reference object to be measured immediately before or substantially simultaneously with pressure measurement on the object to be measured, and comparing a measurement value of the reference object to be measured with a measurement value of the object to be measured to measure a pressure of the object to be measured.

A second aspect of the present invention is provided a pressure measuring device, including:

contact means for making contact with the object to be measured, in which the object to be measured has a predetermined shape and a pressure is applied in an outward direction from the object to be measured;

vibration means which is connected with the contact means and vibrated by an application of a voltage;

voltage applying means for applying an alternating current voltage to the vibration means;

measuring means for measuring a current value flowing through the vibration means; and information processing means for calculating a pressure value corresponding to the current value measured by the measuring means, wherein, when the alternating current voltage is applied to the vibration means by the voltage applying means while the vibration means is in contact with the object to be measured through the contact means, the current value flowing through the vibration means is measured by the measuring means, and the pressure of the object to be measured is calculated by the information processing means.

A third aspect of the present invention is provided a tonometer, including:

contact means for making contact with an eyeball indirectly;

vibration means which is connected with the contact means and vibrated by an application of a voltage;

voltage applying means for applying an alternating current voltage to the vibration means;

measuring means for measuring a current value flowing through the vibration means; and information processing means for calculating a pressure value corresponding to the current value measured by the measuring means, wherein, when the alternating current voltage is applied to the vibration means by the voltage applying means while the vibration means is in contact with the eyeball through the contact means, the current value flowing through the vibration means is measured by the measuring means, and the intraocular pressure of the eyeball is calculated by the information processing means.

In the second and third aspect of the inventions, in a typical case, a resonance point of the object to be measured is calculated based on a change in the measured current value which is caused by a change in vibration frequency, and a current value at a region of the resonance point is measured.

In the second and third aspect of the present inventions, in a typical case, support means is further provided outside a movable region of the contact means and a movable region of the vibration. means.

In the second and third aspect of the inventions, it is suitable to employ a structure in which pressure measurement on the reference object to be measured which a reference for correcting a change in measurement value which is caused by a temperature characteristic of the vibrator is executed immediately before pressure measurement or intraocular pressure measurement on the object to be measured and a measurement value of the reference object to be measured is compared with a measurement value of the object to be measured by the calculating means to measure the pressure of the object to be measured.

In the second and third aspect of the inventions, it is suitable to further include outputting means for outputting a result obtained by the measuring means and/or a result obtained by the calculating means. In the present invention, the contact means is typically connected with the vibration means through a holding member. It is desirable to use an elastic body such as a rubber as the holding member.

The technical idea of the present invention is not necessarily limited to a combination of those described above. Thus, technical ideas realized by an arbitrary suitable combination of the above-mentioned plural aspects of the present invention are also involved.

Effects of the Invention

As described above, according to the pressure measuring method of the present invention, the pressure of the object to be measured which has the predetermined shape and from which the pressure is applied outward can be measured with high reproducibility by a simple method.

According to each of the pressure measuring device and the tonometer of the present invention, an inner pressure for maintaining a shape of the object to be measured or an intraocular pressure can be measured by merely making slight contact with the object to be measured or the eyeball through the eyelid. Therefore, the pressure can be accurately measured by a simple method without large influence on the object to be measured.

According to the tonometer of the present invention, the intraocular pressure can be accurately measured by a simple method without influence on the eyeball. Therefore, the intraocular pressure can be accurately measured by a person to be examined with safety without causing the person to be examined to feel discomfort.

BRIEF DESCRIPTION OF THE DRAWINGS

FIG. 1 is a diagram showing a structure of a pressure measuring device according to an embodiment of the present invention;

FIG. 2 is a schematic line view showing a measurer used for intraocular pressure measurement in the embodiment of the present invention;

FIG. 3A is schematic line view showing a bimorph type vibrator included in the measurer in the embodiment of the present invention;

FIG. 3B is schematic line view showing a bimorph type vibrator included in the measurer in the embodiment of the present invention;

BEST MODE FOR CARRYING OUT THE INVENTION

Figure 4B:
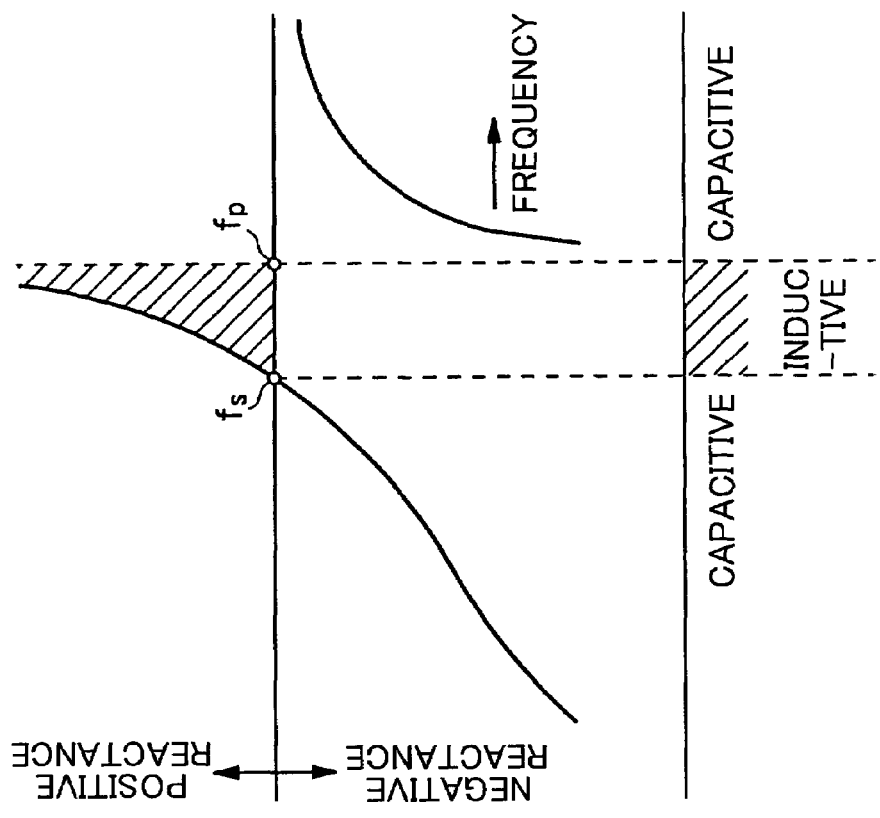
FIG. 4B is a frequency-impedance characteristic of the vibrator in the embodiment of the present invention.

Hereinafter, an embodiment of the present invention will be described with reference to the accompanying drawings. Note that the same or corresponding portions in each of the drawings for the following embodiment are denoted by the same reference symbols.

First, a pressure measuring device according to the embodiment of the present invention will be described. FIG. 1 shows the entire structure of the pressure measuring device according to this embodiment.

As shown in FIG. 1, the pressure measuring device according to the embodiment of the present invention, which is used as a tonometer, includes a measurer 1 for actually measuring an intraocular pressure, a piezoelectric driver 2, a terminal base 3, an information processing device 4, and a resistor 5.

The piezoelectric driver 2 is used to amplify an applied voltage. The terminal base 3 is used to concentrate input and output wirings, apply to the measurer 1 the voltage amplified by the piezoelectric driver 2 as an output, and measure a potential or voltage which is an input. Note that the piezoelectric driver 2 is constructed such that a voltage outputted from the terminal base 3 can be amplified by, for example, 15 times. The resistor 5 is used to cause voltage drop between both end portions of the resistor 5 and a resistance value thereof is, for example, 1 kΩ in this embodiment.

The information processing device 4 includes an information processing section and an auxiliary storage section which compose calculating means such as a personal computer having, for example, a hard disk. The information processing device 4 further includes a display capable of outputting a result obtained by calculation and a result obtained by measurement, serving as outputting means. In this embodiment, the personal computer is used for the information processing device 4. However, each device including an information processing section capable of performing information processing such as calculation processing and a storage section can be employed and thus the information processing device 4 is not necessarily limited to the personal computer.

The auxiliary storage section (not shown) included in the information processing device 4 has an operating system (OS) 4a for operating the information processing device 4, serving as a base, an information storage database 4b, a measurement result processing application 4c, an input data analysis program 4d, a calculation processing application 4e, and an output side frequency change program 4f, which are installed therein. The information processing device 4 executes various analysis processings and calculation processings based on the programs. In examples described later, measurement processing and analysis processing are executed based on the programs.

(Measurer)

Next, the measurer 1 used for the pressure measuring device according to this embodiment will be described. FIG. 2 shows the measurer 1 and FIG. 3 shows an example of a bimorph type vibrator used for the measurer 1.

As shown in FIG. 2, the measurer 1 according to this embodiment has a structure for bringing a contactor 14 into contact with an eyelid 16 during intraocular pressure measurement. The measurer 1 includes a vibrator 11 serving as vibrating means, such as a bimorph type vibrator, four rubber bases 12 serving as elastic bodies, a case 13 vibratable with the vibrator 11 and the rubber bases 12 housed therein, and the contactor 14 for making actual contact with the eyelid 16. Therefore, the vibrator 11 is substantially in indirect contact with an eyeball 17, so the eyeball 17 is vibrated with the vibrator 11.

The vibrator 11 is held on both sides by two pairs of rubber bases 12, so it is located and fixed in the center of the case 13. As shown in FIG. 3, the vibrator 11 has a structure in which a metallic plate 11b is sandwiched on both sides by ceramic elements 11a. The vibrator 11 is electrically connected with the piezoelectric driver 2 (not shown in FIG. 3) through a vibrator cable 15.

In the measurer 1 having the above-mentioned structure, when a voltage is applied from an outside to the vibrator 11 through the vibrator cable 15, the vibrator 11 first vibrates. Then, the vibration passes through the rubber bases 12, the case 13, and the contactor 14, so the entire case 13 vibrates to transfer the vibration to the eyeball 17 through the contactor 14 and the eyelid 16. That is, the measurer 1 in this embodiment is used to provide the vibration to the eyeball to be examined and noninvasively measure vibration of the eyeball to be examined. Note that the word "noninvasively" indicates that a member which is in direct contact with a cornea (not specifically shown) of the eyeball 17 is not used.

(Intraocular Pressure Measurement Principle)

Next, a measurement principle in the case where an intraocular pressure is measured using the pressure measuring device having the above-mentioned structure will be described.

That is, as a result of experiments and concentrated studies, the inventors of the present invention found that the vibrator 11 provided in the measurer 1 has a characteristic that, while a predetermined alternating current voltage is being applied to continuously drive the vibrator, a current flowing through the vibrator is changed corresponding to a state of an object to be measured, which is in contact with the vibrator 11 through the contactor 14. Here, experiments and studies on a bimorph type vibrator used as the vibrator 11 will be described below.

(Bimorph Type Vibrator)

Figure 4A:
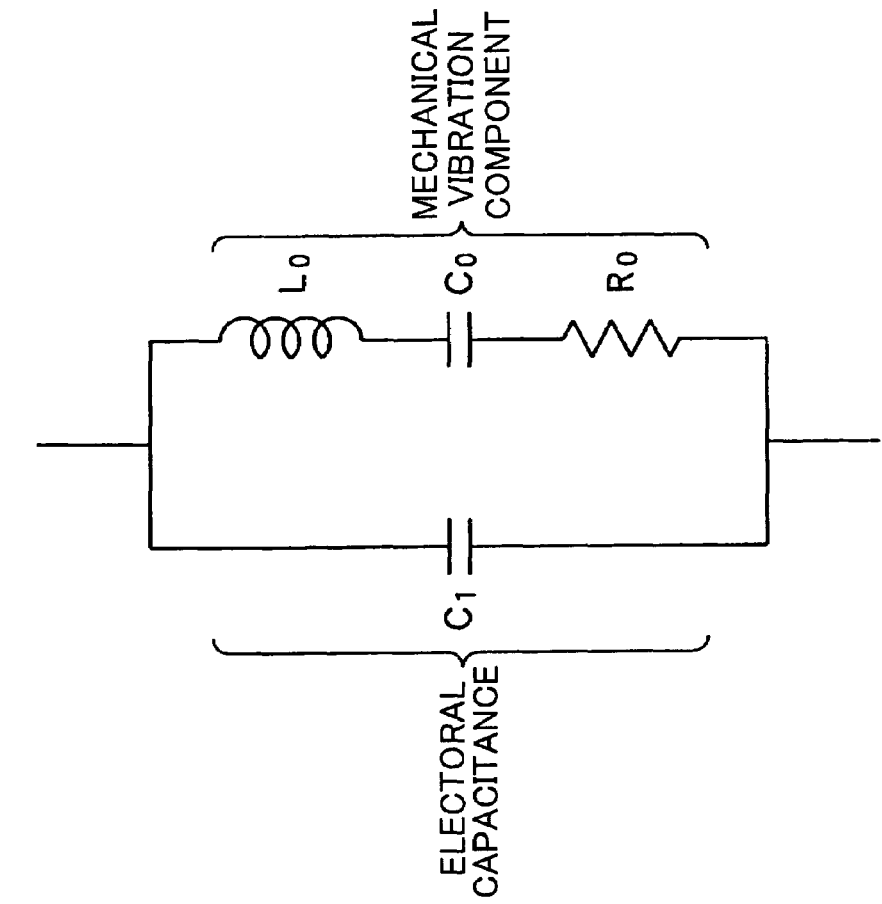
FIG. 4A is diagram showing an equivalent circuit of a vibrator in the embodiment of the present invention.

The vibrator 11 can be represented by an equivalent circuit shown in FIG. 4A. This equivalent circuit is an equivalent circuit of the vibrator 11 in a non-contact state. Even when the vibrator 11 is in contact with an arbitrary object, the same equivalent circuit can be fundamentally obtained. FIG. 4B shows a frequency-impedance characteristic of the equivalent circuit.

As is apparent from FIG. 4B, the vibrator 11 resonates in parallel and an impedance thereof is changed according to a frequency of an applied voltage. Therefore, it is apparent that, when the applied alternating current voltage is continuously maintained to a predetermined voltage, a current flowing through the vibrator 11 is changed according to the frequency. In FIG. 4B, fs which is one of resonance points is a mechanical resonance point of the vibrator 11 and fp which is the other of the resonance points is a resonance point caused by the vibrator 11.

The measurer 1 including the vibrator 11 is placed on a rubber vibration isolator (not shown). Other vibrator cables and the like are set. After that, the vibrator 11 is irradiated with laser light at each measurement frequency to measure a vibration amplitude thereof using a laser displacement meter. The frequency of the applied voltage is set to 400 Hz to 700 Hz at intervals of 10 Hz. The measurement frequency is set to the vicinity of a resonance point determined in advance, more specifically, in a frequency range close to the resonance point.

As a result of measurement, it is found that a characteristic value and a resonance frequency are shifted according to the hardness of a material. As described above, the vibrator 11 resonates in parallel and the impedance thereof is changed according to the frequency of the applied voltage. That is, when the applied alternating. current voltage is continuously maintained to the predetermined voltage, the flowing current is changed according to the frequency. Therefore, this characteristic is utilized. A current flowing through the vibrator 11 is measured from a voltage dropped across the resistor 5 connected in series with the vibrator 11. An intraocular pressure is calculated based on the measured current value.

(Intraocular Pressure Measuring Method)

To be specific, first, the measurer 1 is placed so as to be in contact with the eyeball 17 through the eyelid 16. Next, an alternating current voltage is applied to the vibrator 11 based on the frequency change program installed in the information processing device 4. When the vibrator 11 is vibrated by the application of the alternating current voltage, the entire measurer 1 vibrates. The vibration is transferred to the eyeball 17 through the eyelid 16. When the vibration is transferred to the eyeball 17, the eyeball 17 also generates vibration corresponding to the intraocular pressure thereof, thereby changing a vibration amplitude of the measurer 1. Therefore, the amplitude of the vibrator 11 changes and the current flowing through the vibrator 11 is changed by a change in amplitude thereof.

Then, potentials at both ends of the resistor 5 are measured and the measured potential values are inputted to the information processing device 4. The information processing device 4 performs calculation processing on the potential values based on the calculation processing application to obtain a difference therebetween, that is, a voltage. Therefore, a change in current flowing through the vibrator 11 is calculated. An intraocular pressure value is calculated based on the current value by the information processing device 4. Because the information processing device 4 includes the display serving as the outputting means, when the change in current is calculated, a result obtained by analysis processing using the analysis program is displayed on the display.

Hereinafter, although specific methods of embodying the present invention will be described with reference to examples, the present invention is not limited to those.

EXAMPLE 1

Figure 5A:
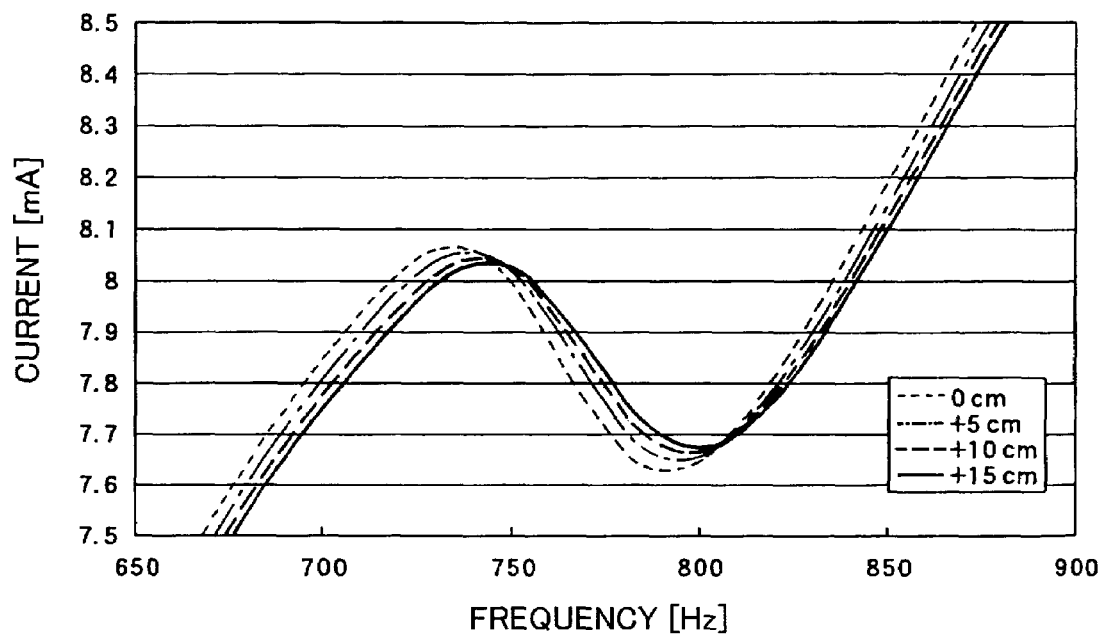
FIG. 5A is graph showing frequency-current characteristic results obtained by changing an inner pressure of a balloon filled with water using an intraocular pressure measuring. method according to an embodiment of the present invention.
Figure 5B:
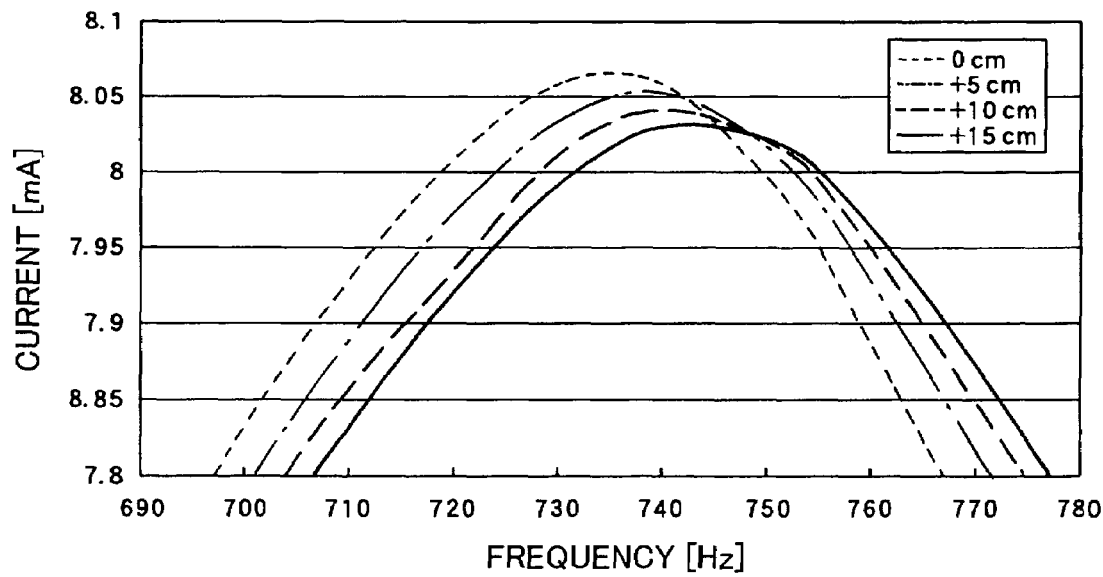
FIG. 5B is graph showing frequency-current characteristic results obtained by changing an inner pressure of a balloon filled with water using an intraocular pressure measuring method according to an embodiment of the present invention.

A rubber balloon filled with water, which is a model of the eyeball, is attached to an end of a cylindrical glass tube. The cylindrical glass tube is fixed to a support base. The contactor 14 of the measurer 1 is made in contact with the balloon and water is slowly injected to the glass tube to change an inner pressure of the balloon. At this time, a level increased from an interface portion between the balloon and the glass tube by 1 cm is set as a reference. A level of the water is increased from the reference to 5 cm, 10 cm, and 15 cm at intervals of 5 cm to change the inner pressure of the balloon. FIG. 5 shows a frequency characteristic of a result obtained by measurement. FIG. 5B is an enlarged graph showing the region of resonance points in a frequency range shown in FIG. 5A.

As is apparent from FIG. 5, when the measurer 1 is made in contact with the rubber balloon to perform measurement, a current characteristic can be obtained in order of pressure and the resonance points of the vibrator 11 exist in a frequency region of 700 Hz to 850 Hz. As is also apparent from the figure, the current characteristic reduces with an increase in pressure in a frequency range outside the frequency region between the two resonance points. In contrast to this, the current characteristic increases with an increase in pressure in the frequency region between the two resonance points. That is, as is apparent from that, in the case of a mechanical resonance, the current reduces with an increase in inner pressure of the balloon. In the case of a resonance based on an electrical capacitance, the current increases with an increase in pressure. As is apparent from that, when the inner pressure is changed, a changed pressure can be determined using the measurer 1.

EXAMPLE 2

Next, a frequency-current characteristic of an eyeball with an eyelid, of a pig (pig eye with eyelid) in the case where an inner pressure of the eyeball thereof is changed is measured. An intraocular pressure changing method to be employed is a method of inserting an injection needle from optic nerves of the pig eye, connecting the injection needle with a container containing a normal saline solution, and moving the container upward and downward with a state in which a water surface level of the container is made substantially equal to a level of the pig eye, thereby changing an intraocular pressure of the pig. Then, the eyelid of the pig eye with eyelid is opened and the measurer 1 is made in direct contact with the eyeball. The measurement is performed in a frequency region of 700 Hz to 850 Hz. After that, the eyelid is closed and the same measurement is performed in contact with the eyelid. A series of measurement described above is repeated while the intraocular pressure is changed.

Figure 6A:
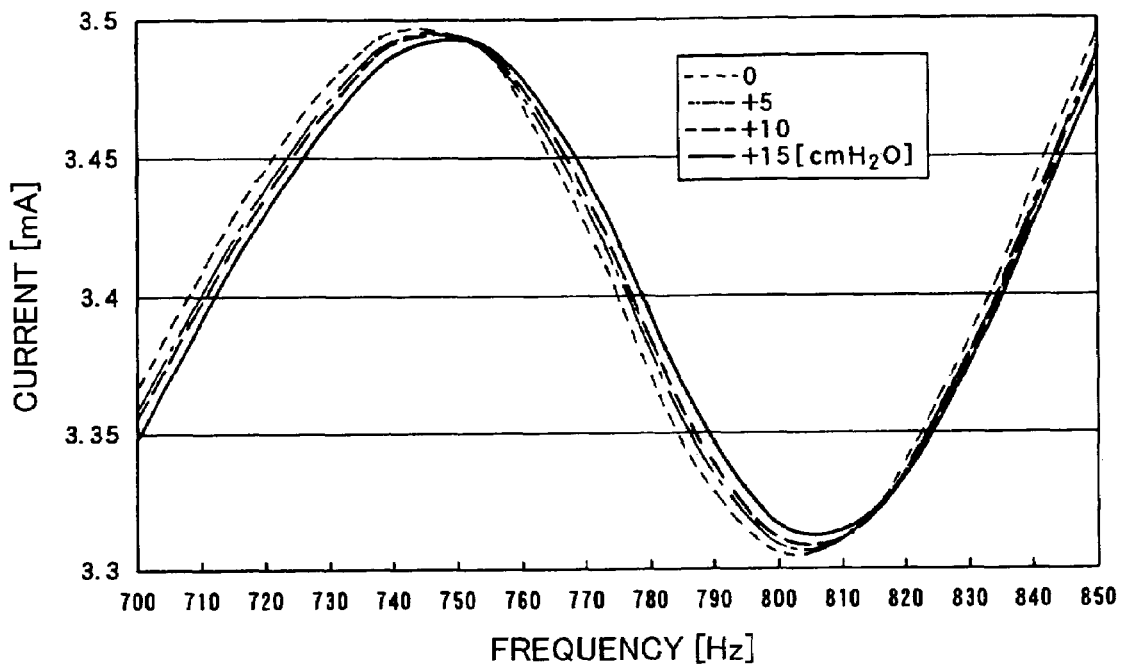
FIG. 6A is graph showing results obtained by measuring an intraocular pressure in a state in which the measurer in the embodiment of the present invention is made in direct contact with a pig eye.
Figure 6B:
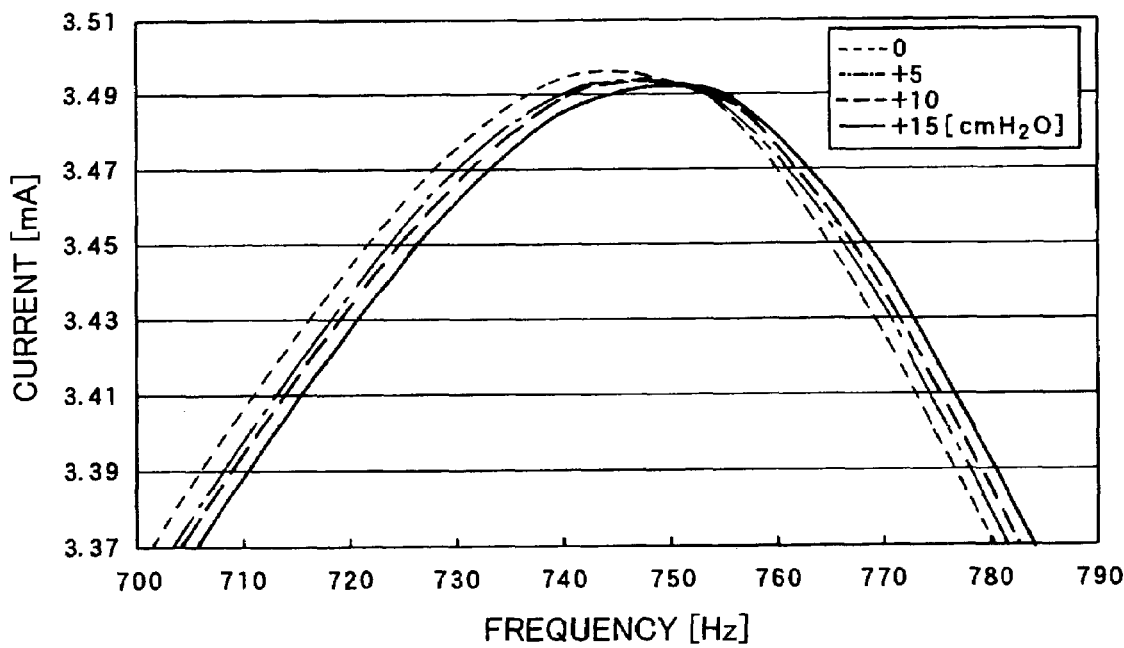
FIG. 6B is graph showing results obtained by measuring an intraocular pressure in a state in which the measurer in the embodiment of the present invention is made in direct contact with a pig eye.
Figure 7A:
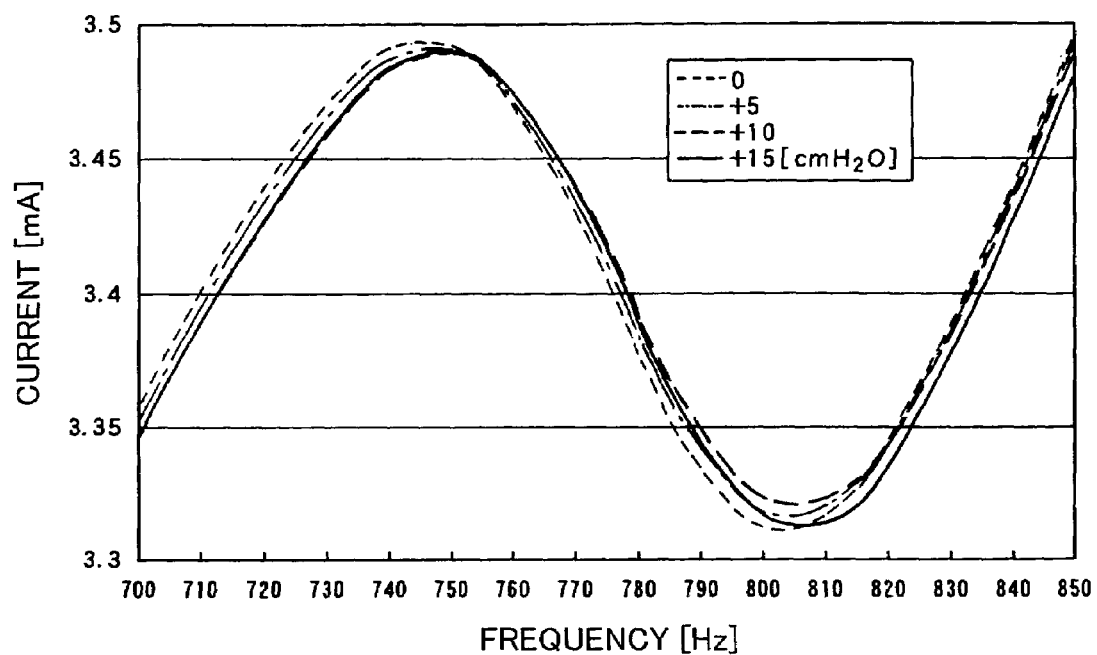
FIG. 7A is graph showing results obtained by measuring an intraocular pressure in a state in which the measurer in the embodiment of the present invention is made in contact with the pig eye through an eyelid thereof.
Figure 7B:
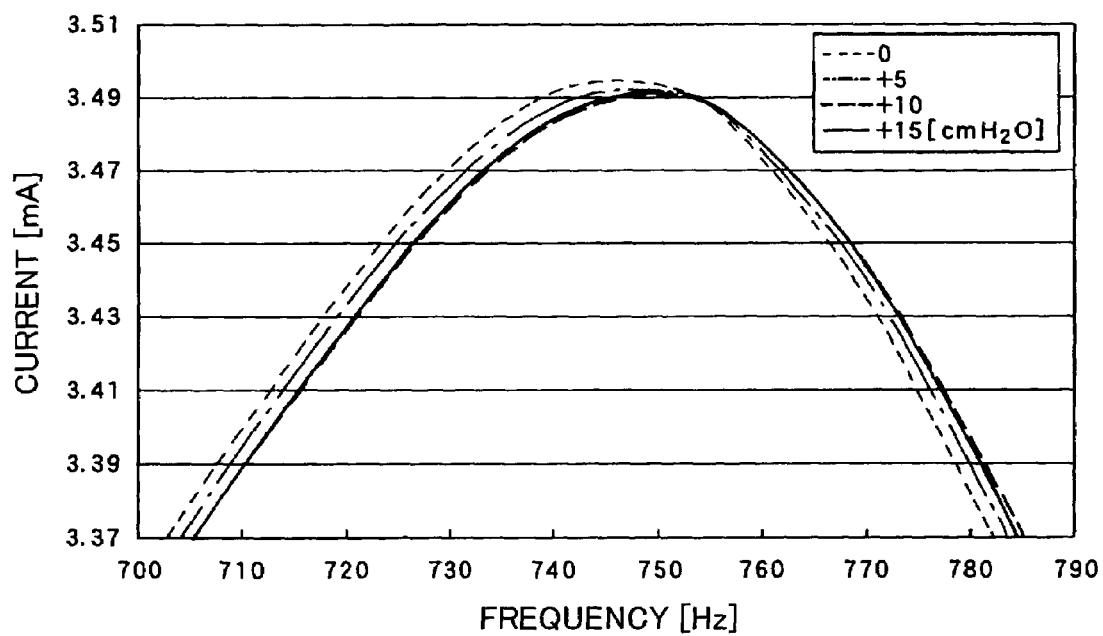
FIG. 7B is graph showing results obtained by measuring an intraocular pressure in a state in which the measurer in the embodiment of the present invention is made in contact with the pig eye through an eyelid thereof.

Results obtained by frequency-current characteristic measurement as described above are shown in FIGS. 6 and 7. FIG. 6 shows a result obtained by measurement in the case where the measurer 1 is made in direct contact with the eyeball. FIG. 7 shows a result obtained by measurement in the case where the measurer 1 is made in contact with the eyelid with a state in which the eyelid is closed. FIGS. 6B and 7B are enlarged graphs showing the regions of resonance points in frequency ranges shown in FIGS. 6A and 7A.

As is apparent from FIGS. 6 and 7, a current characteristic can be obtained in order of pressure by measurement in each of the case where the measurer 1 is made in contact with the eyeball and the case where the measurer 1 is made in contact with the eyelid. In addition, a result in the case of the measurer 1 being in contact with the eyeball is very similar to that in the case of the measurer 1 being in contact with the eyelid.

Figure 8:
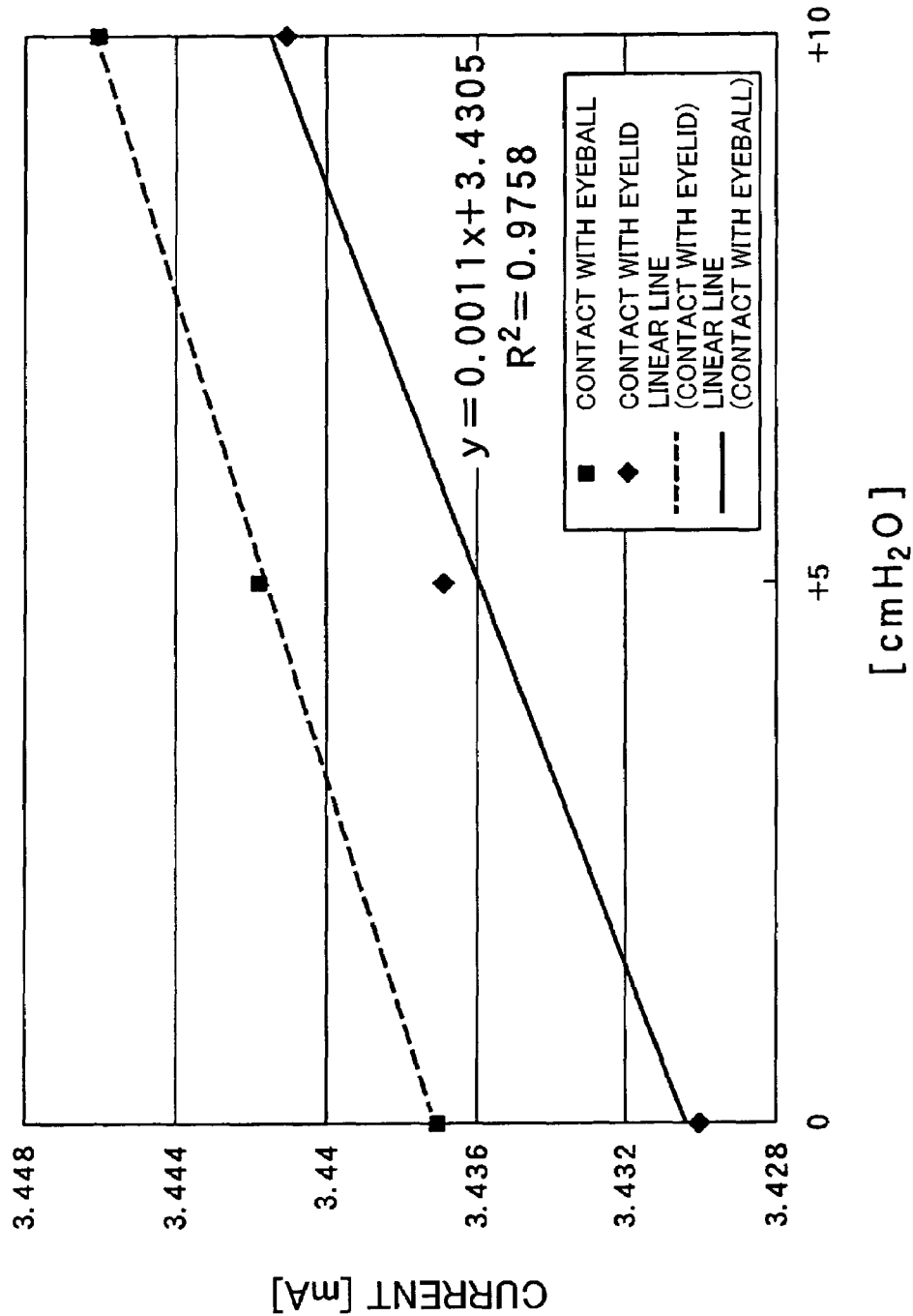
FIG. 8 is graph showing results obtained by a current-pressure characteristic measurement in the case where the measurer in the embodiment of the present invention is made in direct contact with the pig eye and the case where the measurer is made in contact with the pig eye through the eyelid thereof.

Based on the results, FIG. 8 shows a comparison between the result of FIG. 6 and the result of FIG. 7 with respect to the dependence of current value on pressure at a frequency point of 769 Hz (which is an intermediate point between a local maximum point and a local minimum point (i.e., two resonance points)).

As is apparent from FIG. 8, although current shift is caused between the case where the measurer 1 is made in contact with the eyeball and the case where the measurer 1 is made in contact with the eyelid, similar characteristics are obtained. Therefore, it is apparent that the influence of the eyelid 16 is small in the case where the measurer 1 is used in this embodiment.

EXAMPLE 3

In the course of the measurement on the pig eye, the inventors of the present invention found that the vibrator 11 of the measurer 1 has temperature characteristics and a current is varied thereby. Then, the inventors of the present invention devised a method of performing measurement after the vibrator 11 continuously vibrates until a temperature thereof saturates. Therefore, stable intraocular pressure measurement can be performed.

Figure 9A:
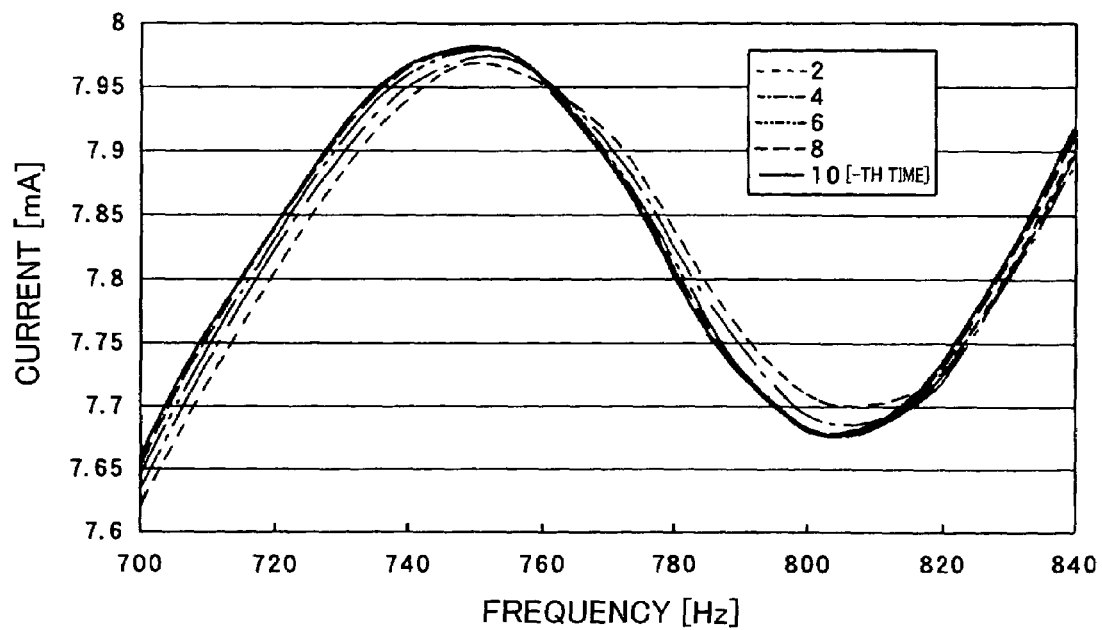
FIG. 9A is graph showing results obtained by a frequency-current characteristic measurement in the case where intraocular pressure measurement on the same person to be examined is performed 10 times using the measurer in the embodiment of the present invention.
Figure 9B:
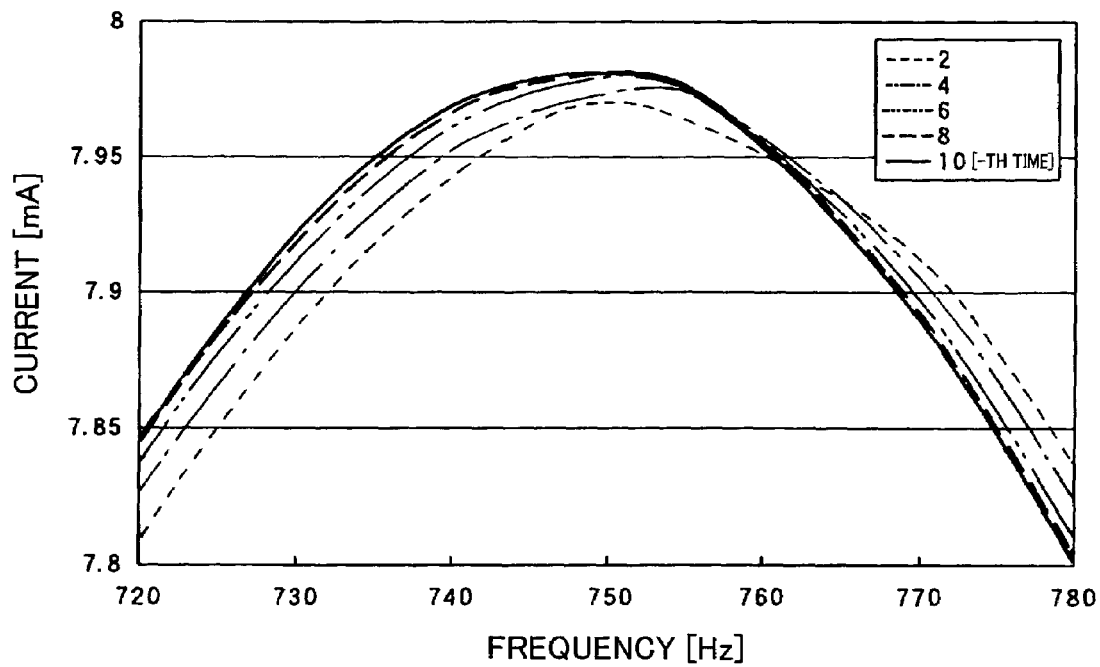
FIG. 9B is graph showing results obtained by a frequency-current characteristic measurement in the case where intraocular pressure measurement on the same person to be examined is performed 10 times using the measurer in the embodiment of the present invention.

This method is employed and current characteristic measurement on the same person to be examined is performed successively using the measurer 1. That is, the vibrator 11 is vibrated for 45 minutes. Immediately after the temperature of the vibrator 11 saturates, the measurer 1 in this embodiment is made in contact with the eyelid of a human and the current characteristic measurement is performed 10 times at intervals of 2 minutes. A frequency region for current characteristic measurement is set to 700 Hz to 840 Hz. The measurer 1 is separated from the eyelid 16 for each measurement. FIG. 9 shows a result obtained by the measurement. FIG. 9B is an enlarged graph showing the region of resonance points in a frequency range shown in FIG. 9A.

As is apparent from FIG. 9, a current increases with an increase in the number of measurement in a frequency range outside the frequency region between two resonance points. As is already apparent from the result in Example 1 as described above, the increase in current in the frequency range outside the frequency region between the two resonance points is equivalent to a reduction in measured pressure. Therefore, it is apparent that the intraocular pressure is changed by the repetition of measurement.

EXAMPLE 4

Figure 10:
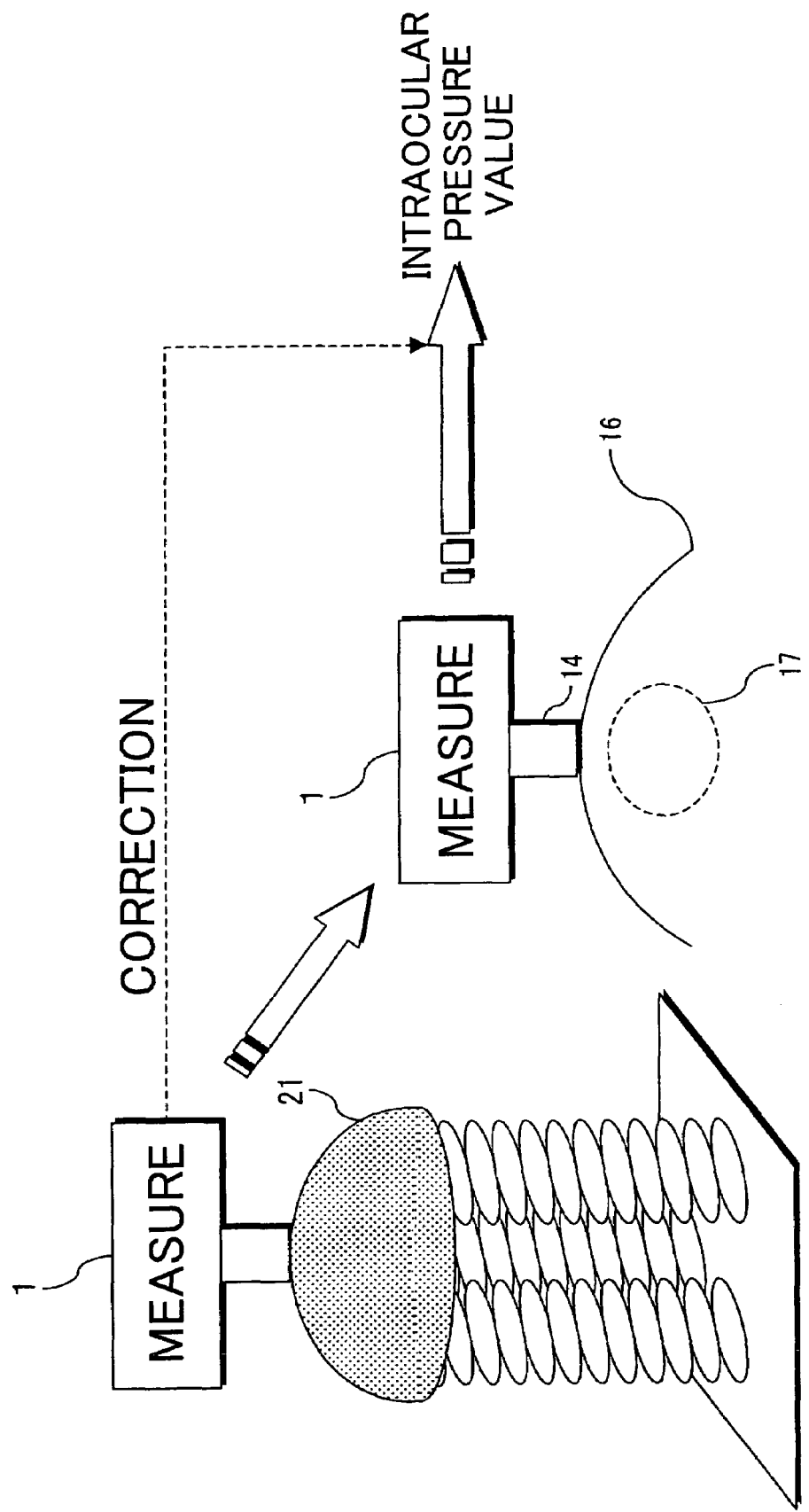
FIG. 10 is a schematic line view to explain a calibration method for intraocular pressure measurement in the embodiment of the present invention.

The method of vibrating the vibrator 11 until the temperature thereof saturates, which is employed for the above-mentioned current characteristic measurement, takes time. The reason is that the vibrator 11 has the temperature characteristic. Then, as a result of study of a method of minimizing the influence of the temperature characteristic, the inventors of the present invention devised a method of performing calibration using a reference base. FIG. 10 shows a calibration procedure using the reference base.

As shown in FIG. 10, a reference base 21 is made of, for example, rubber and is provided on an elastic spring 22 having the same elasticity as that in the case where the eyeball is pressed. The contactor 14 of the measurer 1 is made in contact with an upper portion of the reference base 21 to perform measurement. Immediately after that, the contactor 14 of the measurer 1 is made in contact with the eyelid 16 to measure an intraocular pressure. That is, measurement on the reference base 21 for which a predetermined pressure is continuously maintained and measurement on an eyeball to be examined which is an object to be measured are substantially simultaneously performed. To be specific, the measurements are successively performed in tandem. Therefore, a value measured in contact with the eyelid to perform analysis for obtaining the intraocular pressure is calibrated based on a value measured using the reference base 21 to improve the precision of measurement.

To be specific, a gain a of α value "y" obtained in the case of contact with the eyelid relative to a value "x" obtained in the case where the contactor 14 is made in contact with the reference base 21, at each frequency is calculated using the following expression (1).

$$\alpha = y/x \qquad (1)$$

The gain α in the expression (1) is a ratio between a predetermined pressure continuously applied to the reference base 21 and a measured pressure from the eyelid 16. The pressure applied to the reference base 21 is maintained constant, so the measured pressure becomes constant. Therefore, an intraocular pressure value measured from the eyelid 16 can be accurately obtained based on the gain α. The measurement on the reference base 21 and the measurement on the eyelid 16 are substantially simultaneously performed, so the influence of the temperature characteristic can be minimized.

EXAMPLE 5

Figure 11:
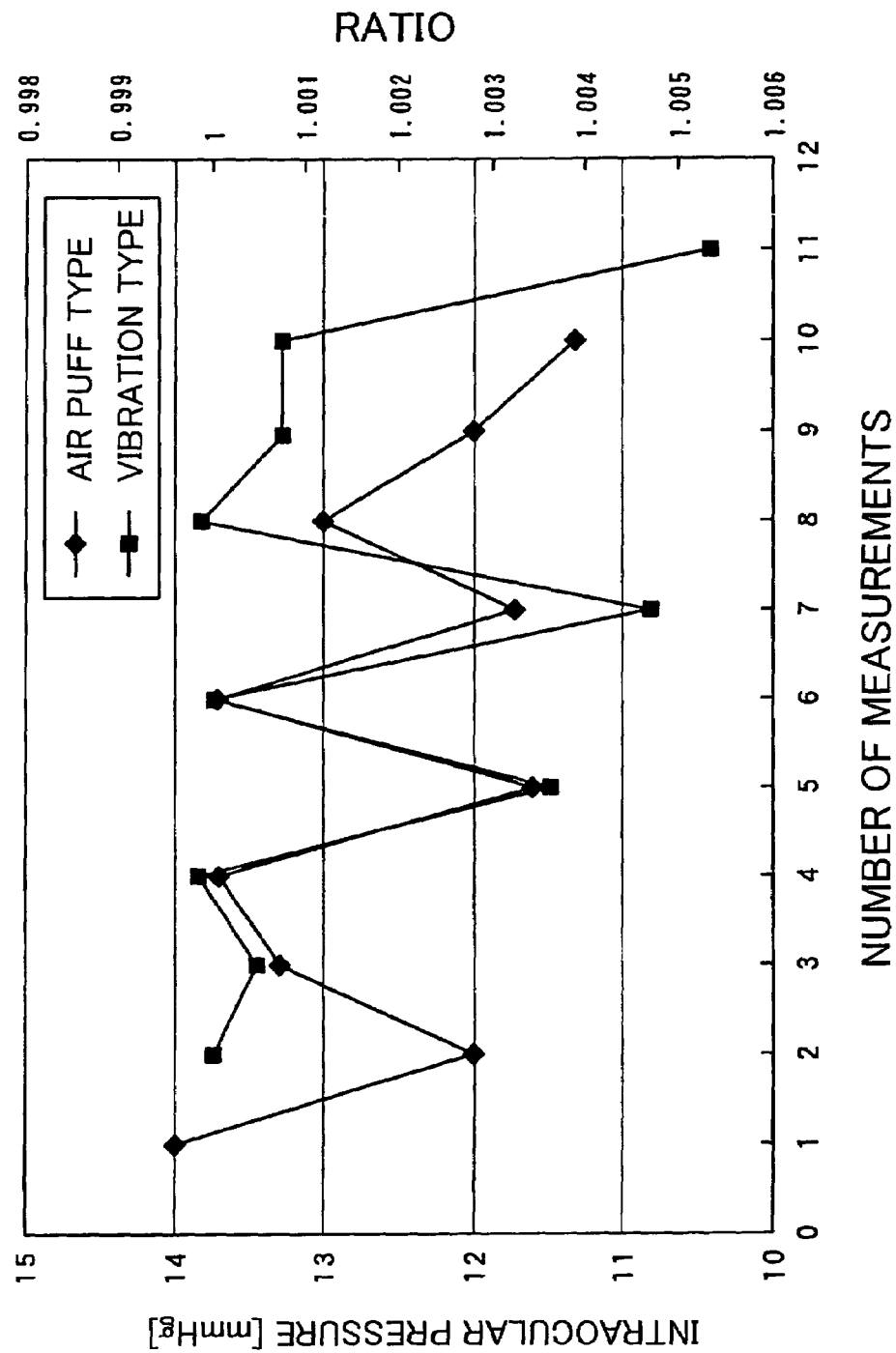
FIG. 11 is a graph showing a change in result obtained by measurement in the case where an intraocular pressure of a human is measured using the measurer in the embodiment of the present invention and a conventional air puff type tonometer.

The inventors of the present invention conducted intraocular pressure measurement with a state in which the measurer 1 in this embodiment is made in contact with the eyelid of a human based on the above-mentioned calibration. The inventors of the present invention conducted intraocular pressure measurement on the eyeball of the human using a conventional air puff type tonometer, as a comparative example. FIG. 11 shows a result obtained by the measurement. As shown in FIG. 11, a measurement number in the case where the measurer 1 is used is shifted by one from a measurement number in the case where the conventional air puff type tonometer is used. This is to meet a change in intraocular pressure which is caused by the successive measurements, which is determined in

EXAMPLE 3

As is apparent from FIG. 11, a change intraocular pressure in the intraocular pressure measurement using the measurer 1 in this embodiment follows that in the measurement using the conventional air puff type tonometer, so substantially the same results are obtained.

Figure 12:
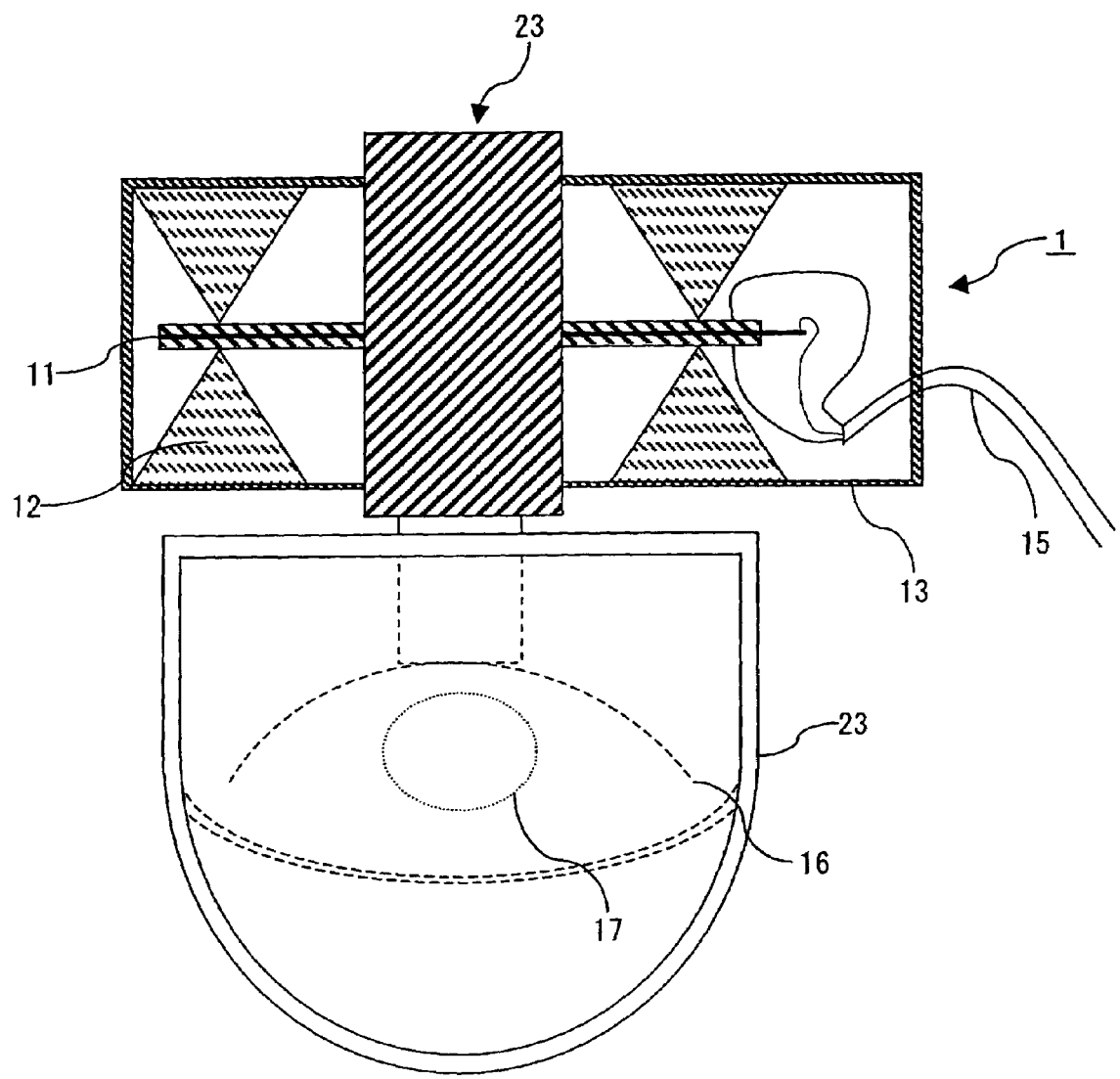
FIG. 12 is a schematic line view showing the measurer provided with a support base in the embodiment of the present invention.
Figure 13:
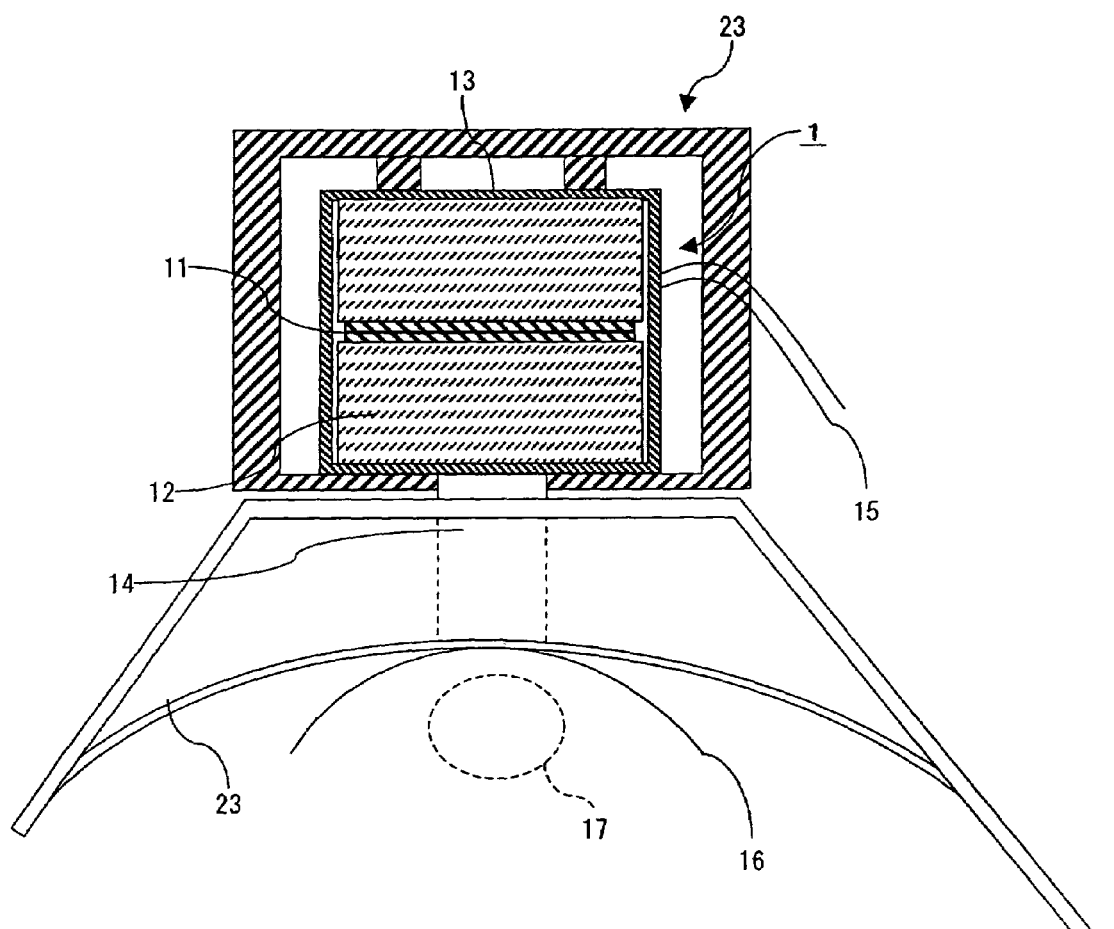
FIG. 13 is a schematic line view showing the measurer provided with the support base in the embodiment of the present invention.

From the above-mentioned examples, the inventors of the present invention found that, in order to use the measurer 1 in this embodiment for a tonometer in which reproducibility is further improved, it is necessary to bring the measurer 1 into contact with the eyelid of a human in the same condition for each contact. However, when the contactor 14 of the measurer 1 is to be made in contact with the eyelid of the human to perform the measurement, it is difficult to place the case 13 of the measurer 1 on the eyelid of the human. Then, as a result of study, the inventors of the present invention devised to provide a support base for supporting the case 13 of the measurer 1. FIGS. 12 and 13 show a structure of the measurer 1 provided with the support base.

As shown in FIGS. 12 and 13, a support base 23 supports the case 13 and has a concave curve-shaped portion close to a skeletal shape of the vicinity of an eye of the human, which is provided therein. In this embodiment, the support base 23 is formed such that a side shown in FIG. 12 corresponds to the left side or the right side of the face of the human. In addition, the support base 23 is formed such that a left side shown in FIG. 13 corresponds to a nose side relative to the eye and a right side shown therein corresponds to a temple side relative to the eye. Therefore, the support base 23 is constructed to support the measurer 1 and cover the vicinity of the eye in the face of the human. When the concave curve-shaped portion of the support base 23 is made in contact with the vicinity of the eyeball of the human, the contactor 14 is in contact with the eyelid 16. In order to prevent the support base 23 from influencing the intraocular pressure measurement, the support base 23 is held in the outside of the case 13 and attached to a portion which is located outside a movable region (i.e., vibration region) of the contactor 11 and does not hinder the vibration.

Therefore, when a user of the measurer 1 holds the support base 23 to measure the intraocular pressure, there is no case where a hand of the user is contact with the contactor 14, the case 13 housing the vibrator 11, or the like during vibration. Thus, the measurement using the measurer 1 is not influenced. The contactor 14 is relatively held to the support base 23, so it is possible to bring the contactor 14 into contact with the eyelid of the human constantly in the same condition.

The embodiment of the present invention and the examples thereof are specifically described. However, the present invention is not limited to the above-mentioned embodiment and thus various modifications based on the technical idea of the present invention can be made.

For example, numerical values described in this embodiment are merely examples and different numerical values may be used if necessary.

For example, in the above-mentioned embodiment, the bimorph type vibrator is employed as the vibrator for the measurer 1. Any vibrator in which a current value is changed according to the amplitude of the vibration can be employed as such a vibrator. For example, a piezoelectric ceramic vibrator such as a Langevin type vibrator can be employed.

In the above-mentioned embodiment, the elastic rubber which is the elastic body is used as a holding member for holding the vibrator 11 in the case 13. However, an elastic spring or a synthetic resin can be also used, for example. Other materials capable of holding the vibrator by a suitable force also can be used.

Further, for example, in order to generate a larger vibration in the vibrator 11 provided in the measurer 1 in the above-mentioned embodiment, a weight made of, for example, brass, stainless steel, or metal such as lead (Pb) or copper (Cu) may be further provided in the vibrator 11. The weight can be provided in an arbitrary portion of the vibrator 11. In view of the stability of vibration, it is desirable to provide the weight in a center portion of the vibrator 11 on a surface perpendicular to a vibration amplitude direction thereof.

Description of Symbols 1 measurer
2 piezoelectric driver
3 terminal base
4 information processing device
4a operating system
4b information storage database
4c measurement result processing application
4d input data analysis program
4e calculation processing application
4f output side frequency change program
5 resistor
11 vibrator
11a ceramic element
11b metallic plate
12 rubber base
13 case
14 contactor
15 vibrator cable
16 eyelid
17 eyeball
21 reference base
22 elastic spring
23 support base

What is claimed is:

1. A pressure measuring device, comprising:
contact means for making contact with an object to be measured, in which the object to be measured has a predetermined shape and a pressure is applied in an outward direction from the object to be measured;
vibration means which is connected with the contact means and configured to vibrate at a plurality of frequencies upon application of a voltage signal;
voltage applying means for applying the voltage signal to the vibration means;
measuring means for measuring a current flowing through the vibration means at the plurality of frequencies; and
information processing means for determining two resonance points of a system including the object to be measured and for determining the pressure based on the current measured by the measuring means at the plurality of frequencies, wherein the information processing means determines that a first pressure is higher than a second pressure by determining that the first pressure has a lower measured current than the second pressure at frequencies outside a frequency range between the two resonance points and by determining that the first pressure has a higher measured current than the second pressure at frequencies within the frequency range between the resonance points.

2. A pressure measuring device according to claim 1, further comprising support means,
wherein the support means is provided outside a movable region of the contact means and a movable region of the vibration means.

3. A pressure measuring device according to claim 1, further comprising calibration means for minimizing the influence of temperature on the determination of pressure.

4. A tonometer, comprising:
contact means for making contact with an eyeball indirectly;
vibration means which is connected with the contact means and configured to vibrate at a plurality of frequencies upon application of a voltage signal and configured to vibrate at a plurality of frequencies upon application of a voltage signal;
voltage applying means for applying the voltage signal to the vibration means;
measuring means for measuring a current value flowing through the vibration means at a plurality of frequencies; and
information processing means for determining two resonance points of a system including the object to be measured and for determining the pressure based on the current measured by the measuring means at the plurality of frequencies, wherein the information processing means determines that a first pressure is higher than a second pressure by determining that the first pressure has a lower measured current than the second pressure at frequencies outside a frequency range between the two resonance points and by determining that the first pressure has a higher measured current than the second pressure at frequencies within the frequency range between the resonance points.

5. A tonometer according to claim 4, further comprising support means,
wherein the support means is provided outside a movable region of the contact means and a movable region of the vibration means.

6. A tonometer according to claim 4, further comprising calibration means for minimizing the influence of temperature on the determination of intraocular pressure.

7. A pressure measuring device, comprising:
a contactor configured to contact the surface of an object to be measured, wherein the object to be measured has a predetermined shape and an internal pressure to be measured;
a vibrator connected with the contactor and configured to vibrate at a plurality of frequencies upon application of a voltage signal;
driver circuitry configured to apply the voltage signal to the vibrator;
measurement circuitry configured to measure a current value flowing through the vibrator at the plurality of frequencies; and
an information processing device configured to determine two resonance points of a system including the object to be measured and configured to determine the pressure based on the current measured by the measurement circuitry at the plurality of frequencies, wherein the information processing device determines that a first pressure is higher than a second pressure by determining that the first pressure has a lower measured current than the second pressure at frequencies outside a frequency range between the two resonance points and by determining that the first pressure has a higher measured current than the second pressure at frequencies within the frequency range between the resonance points.

8. A pressure measuring device according to claim 7, further comprising a calibration device configured to minimize the influence of temperature on the determination of pressure.

9. A pressure measuring device according to claim 7, further comprising a reference base having a predetermined pressure.

10. A pressure measuring device according to claim 9, wherein the information processing means is further configured to determine the pressure based on a measurement of the reference base.

* * * * *

UNITED STATES PATENT AND TRADEMARK OFFICE
CERTIFICATE OF CORRECTION

PATENT NO. : 7,713,197 B2  Page 1 of 1
APPLICATION NO. : 11/578910
DATED : May 11, 2010
INVENTOR(S) : Nakai et al.

It is certified that error appears in the above-identified patent and that said Letters Patent is hereby corrected as shown below:

At Column 4, Line 11, delete "vibration." and insert therefore, --vibration--.

At Column 5, Line 10, delete "measuring." and insert therefore, --measuring--.

At Column 7, Line 63, delete "alternating." and insert therefore, --alternating--.

At Column 11, Line 2, delete "EXAMPLE 3" and insert the same on Col. 11, Line 10, after "in" as a continuation.

Signed and Sealed this

Second Day of November, 2010

David J. Kappos
*Director of the United States Patent and Trademark Office*